US00RE49088E

(19) United States
(12) Reissued Patent
Buck, Jr. et al.

(10) Patent Number: US RE49,088 E
(45) Date of Reissued Patent: May 31, 2022

(54) SYSTEMS AND METHODS FOR PURSUIT GOVERNANCE IN A MONITORING SYSTEM

(71) Applicant: BI Incorporated, Boulder, CO (US)

(72) Inventors: James J. Buck, Jr., Berthoud, CO (US); Michael Todd Cooke, Highlands Ranch, CO (US); Joseph P. Newell, Louisville, CO (US)

(73) Assignee: BI Incorporated, Boulder, CO (US)

(21) Appl. No.: 16/440,560

(22) Filed: Jun. 13, 2019

Related U.S. Patent Documents

Reissue of:
(64) Patent No.: 10,101,431
Issued: Oct. 16, 2018
Appl. No.: 15/207,121
Filed: Jul. 11, 2016

U.S. Applications:
(63) Continuation of application No. 14/444,809, filed on Jul. 28, 2014, now Pat. No. 9,423,487.

(60) Provisional application No. 61/970,756, filed on Mar. 26, 2014.

(51) Int. Cl.

| | |
|---|---|
| ***G08B 1/08*** | (2006.01) |
| ***G01S 5/00*** | (2006.01) |
| ***G01S 19/14*** | (2010.01) |
| ***G01S 19/48*** | (2010.01) |
| ***A61B 5/11*** | (2006.01) |

(52) U.S. Cl.
CPC ..... *G01S 5/0027* (2013.01); *G01S 19/14* (2013.01); *G01S 19/48* (2013.01); *A61B 5/1112* (2013.01)

(58) Field of Classification Search
CPC ..... G01S 5/0027; G01S 19/48; G01S 19/14; A61B 5/1112
See application file for complete search history.

(56) References Cited

U.S. PATENT DOCUMENTS

| | | | |
|---|---|---|---|
| 7,930,927 | B2 | 4/2011 | Cooper et al. |
| 8,493,219 | B2 | 7/2013 | Buck et al. |
| 8,576,065 | B2 | 11/2013 | Buck et al. |
| 8,629,776 | B2 | 1/2014 | Buck et al. |
| 8,657,744 | B2 | 2/2014 | Rompa et al. |

(Continued)

OTHER PUBLICATIONS

U.S. Appl. No. 14/966,135, filed Dec. 11, 2015, Donald A. Melton.

(Continued)

*Primary Examiner* — Jeffrey D Carlson
(74) *Attorney, Agent, or Firm* — HDC Intellectual Property Law, LLP

(57) ABSTRACT

Various embodiments of the present invention provide systems and method for supporting enhanced target pursuit. As an example, a system is disclosed that includes a monitoring device including: a location determination circuit and a controller circuit. The location determination circuit is operable to identify a location of the monitoring device. The controller circuit is operable to: receive a request to modify a schedule of location updates from a standard mode schedule to a pursuit mode schedule, where the standard mode schedule calls for updating the location of the monitoring device at a lower rate than the pursuit mode schedule; and cause an increase in the rate of updating and reporting the location in accordance with the request to modify.

43 Claims, 6 Drawing Sheets

(56) References Cited

U.S. PATENT DOCUMENTS

| | | | | |
|---|---|---|---|---|
| 9,240,118 | B2 | 1/2016 | Melton | |
| 9,241,659 | B2 | 1/2016 | Rompa et al. | |
| 9,423,487 | B2 * | 8/2016 | Buck, Jr. | G01S 5/0027 |
| 9,668,095 | B1 | 5/2017 | Newell et al. | |
| 2005/0068169 | A1 * | 3/2005 | Copley | G08B 21/0283 340/539.13 |
| 2007/0171046 | A1 * | 7/2007 | Diem | G06Q 10/00 340/539.13 |
| 2008/0018459 | A1 * | 1/2008 | Derrick | G07C 1/20 340/539.13 |
| 2009/0309709 | A1 * | 12/2009 | Bevacqua | H04W 12/1206 340/426.18 |
| 2011/0154887 | A1 | 6/2011 | Cooper et al. | |
| 2013/0006066 | A1 | 1/2013 | Melton | |
| 2013/0342394 | A1 * | 12/2013 | Leslie | G01S 19/16 342/357.31 |
| 2015/0048948 | A1 | 2/2015 | Buck et al. | |
| 2015/0061864 | A1 | 3/2015 | Buck et al. | |
| 2015/0078622 | A1 | 3/2015 | Buck et al. | |
| 2015/0131085 | A1 | 5/2015 | Cooper et al. | |
| 2015/0228184 | A1 | 8/2015 | Buck et al. | |
| 2015/0279200 | A1 | 10/2015 | Buck et al. | |
| 2015/0327214 | A1 | 11/2015 | Buck et al. | |
| 2016/0306024 | A1 | 10/2016 | Buck et al. | |

OTHER PUBLICATIONS

U.S. Appl. No. 15/495,365, filed Apr. 24, 2017, Newell et al.
U.S. Appl. No. 15/257,249, filed Sep. 6, 2016, Cooper et al.
U.S. Appl. No. 15/280,956, filed Sep. 29, 2016, Buck et al.

* cited by examiner

SYSTEMS AND METHODS FOR PURSUIT GOVERNANCE IN A MONITORING SYSTEM

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATION

The present application is a continuation of U.S. patent application Ser. No. 14/444,809 entitled "Systems and Methods for Pursuit Governance in a Monitoring System", and filed Jul. 28, 2014 by Buck et al.; which in turn claims priority to (i.e., is a non-provisional of) U.S. Pat. App. No. 61/970,756 entitled "Pursuit Mode in a Tracking System", and filed Mar. 26, 2014 by Buck et al. The entirety of both of the aforementioned applications is incorporated herein by reference for all purposes.

BACKGROUND OF THE INVENTION

The present invention is related to monitoring movement, and in particular to systems and methods for supporting target pursuit in a monitoring system.

Large numbers of individuals are currently monitored as part of parole requirements or other requirements. Such monitoring allows a monitoring agency to determine whether the individual is engaging in acceptable patterns of behavior, and where an unacceptable behavior is identified to stop such behavior going forward. In many monitoring systems, the lack of up to date monitoring information limits the ability of a monitoring agency to support a pursuit of an individual operating outside of a defined acceptable pattern of behavior.

Thus, for at least the aforementioned reasons, there exists a need in the art for more advanced approaches, devices and systems for monitoring.

BRIEF SUMMARY OF THE INVENTION

The present invention is related to monitoring movement, and in particular to systems and methods for supporting target pursuit in a monitoring system.

Various embodiments of the present invention provide monitoring systems that include a monitoring device. The monitoring device includes: a location determination circuit and a controller circuit. The location determination circuit is operable to identify a location of the monitoring device, and the controller circuit is operable to: receive a request to modify a schedule of location updates from a standard mode schedule to a pursuit mode schedule, wherein the standard mode schedule calls for updating the location of the monitoring device at a lower rate than the pursuit mode schedule; and cause an increase in the rate of updating and reporting the location in accordance with the request to modify.

This summary provides only a general outline of some embodiments according to the present invention. Many other objects, features, advantages and other embodiments of the present invention will become more fully apparent from the following detailed description, the appended claims and the accompanying drawings and figures.

BRIEF DESCRIPTION OF THE DRAWINGS

A further understanding of the various embodiments of the present invention may be realized by reference to the figures which are described in remaining portions of the specification. In the figures, similar reference numerals are used throughout several drawings to refer to similar components. In some instances, a sub-label consisting of a lower case letter is associated with a reference numeral to denote one of multiple similar components. When reference is made to a reference numeral without specification to an existing sub-label, it is intended to refer to all such multiple similar components.

DETAILED DESCRIPTION OF THE INVENTION

Figure 1A:
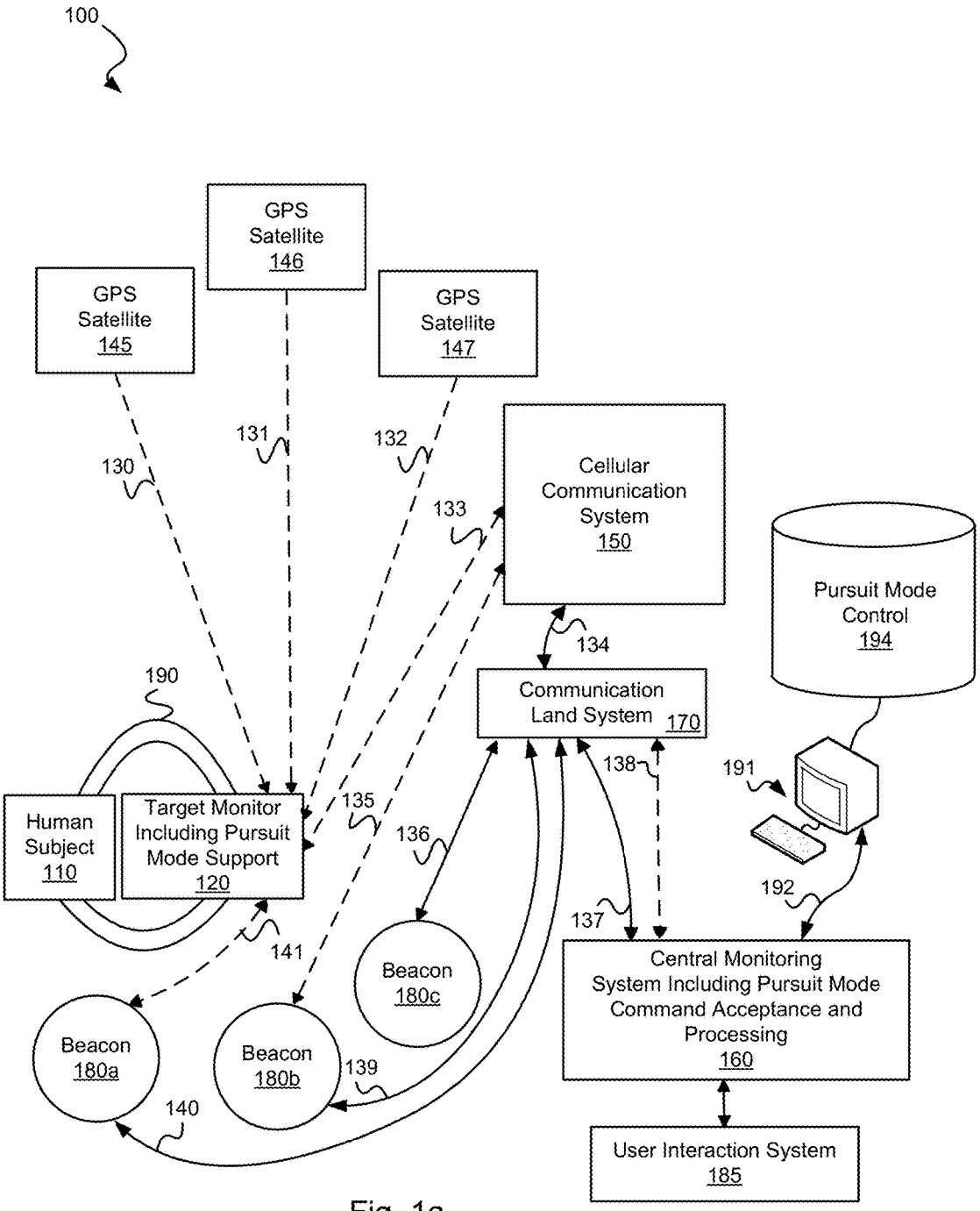
FIG. 1a is a block diagram illustrating a monitoring system including pursuit mode control in accordance with various embodiments of the present invention.

The present invention is related to monitoring movement, and in particular to systems and methods for supporting target pursuit in a monitoring system.

Various embodiments of the present invention provide monitoring systems that include a monitoring device. The monitoring device includes: a location determination circuit and a controller circuit. The location determination circuit is operable to identify a location of the monitoring device, and the controller circuit is operable to: receive a request to modify a schedule of location updates from a standard mode schedule to a pursuit mode schedule, wherein the standard mode schedule calls for updating the location of the monitoring device at a lower rate than the pursuit mode schedule; and cause an increase in the rate of updating and reporting the location in accordance with the request to modify.

In some instances of the aforementioned embodiments, the monitoring system further includes a central monitoring system operable to receive a user request to engage a pursuit mode, and to generate the request to modify for the monitoring device. In some such instances, the central monitoring system is further operable to receive the location from the monitoring device in accordance with the request to modify. In various cases, the central monitoring system is further operable to set a timeout condition corresponding to a maximum duration of operating the monitoring device in accordance with the pursuit mode schedule.

In one or more instances of the aforementioned embodiments, the controller circuit is further operable to modify the schedule of location updates from the pursuit mode schedule back to the standard mode schedule upon expiration of a defined maximum duration of operating the monitoring device in accordance with the pursuit mode schedule. In some such instances, the defined maximum duration is thirty minutes.

In one or more instances of the aforementioned embodiments, the standard mode schedule calls for updating the location every three minutes, and the pursuit mode schedule calls for updating the location every fifteen seconds. In various instances of the aforementioned embodiments, the controller circuit is further operable to: update a power status of the monitoring device; and provide the power status to a central monitoring system. In particular cases, the central monitoring system is operable to: compare the power status of the monitoring device with a threshold value; and provide a power status alert to a user where a combination of a power status being below the threshold value and modification of the schedule of location updates from the standard mode schedule to the pursuit mode schedule has been implemented. In one or more instances of the aforementioned embodiments, the monitor device is attached to a human via a strap. In various cases, the location determination circuit is further operable to identify a direction of movement of the monitoring device, and the direction of movement of the monitoring device is reported when the monitoring device is operating in accordance with the pursuit mode schedule.

Other embodiments of the present invention provide methods for pursuing a monitor target. Such methods include: providing a monitor device associated with a monitor target, wherein the monitor device includes a location detection and update circuit operable to identify a location of the monitor device and to report the location of the monitor device to a central monitoring system; receiving the location of the monitor device in accordance with a standard mode schedule; receiving a request to engage the monitor device in a pursuit mode; commanding the monitoring device to operate in the pursuit mode; and receiving the location of the monitor device in accordance with a pursuit mode schedule, where the standard mode schedule calls for updating the location of the monitoring device at a lower rate than the pursuit mode schedule.

Turning to FIG. 1a, a monitoring system 100 including pursuit mode control is shown in accordance with various embodiments of the present invention. Monitoring system 100 may be tailored for tracking human subjects, however, it should be noted that various implementations and deployments of monitoring system 100 may be tailored for tracking non-human targets such as, for example, other animals or inanimate assets or objects. Such inanimate assets or objects may include, but are not limited to, automobiles, boats, equipment, shipping containers or the like. In one particular embodiment, monitoring system 100 is tailored for tracking delivery vehicles. Based upon the disclosure provided herein, one of ordinary skill in the art will recognize a variety of individuals, animals and/or assets that may be monitored in accordance with different embodiments of the present invention, and/or different monitoring scenarios or systems that may be modified to incorporate one or more features disclosed herein.

Monitoring system 100 includes, but is not limited to, a target monitor 120 that is physically coupled to a human subject 110 by a securing device 190. In some cases, securing device 190 is a strap that includes a tamper sensor 151 that may be, but is not limited to, a continuity sensor that when broken indicates an error or tamper condition. Further, in some cases, tamper sensor 151 may be implemented as a proximity sensor that is able to detect when it has been moved away from an individual being monitored. When such movement away from the individual is detected, an error or tamper condition may be indicated. Based on the disclosure provided herein, one of ordinary skill in the art will recognize a variety of tamper sensors that may be incorporated in either target monitor 120 or securing device 190 to allow for detection of removal of target monitor 120 or other improper or unexpected meddling with target monitor 120. Further, based upon the disclosure provided herein, one of ordinary skill in the art will recognize a variety of monitors and/or securing devices that may be appropriate where the target of the monitoring is not a human or other animal subject, but rather an asset.

Target monitor 120 is designed to provide the location of human subject 110 under a number of conditions. For example, when target monitor 120 is capable of receiving wireless GPS location information 130, 131, 152 from a sufficient number of GPS satellites 145, 146, 147 respectively, target monitor 120 may use the received wireless GPS location information to calculate or otherwise determine the location of human subject 110. Alternatively or in addition, the location of a beacon 180 that is local to target monitor 120 may be used as the location of target monitor 120. As yet another alternative, an AFLT (i.e., advanced forward link trilateration) fix may be established based on cellular communication with target monitor 120. It should be noted that other types of earth based triangulation may be used in accordance with different embodiments of the present invention. Based on the disclosure provided herein, one of ordinary skill in the art will recognize other types of earth based triangulation that may be used.

As yet another alternative, an AFLT fix may be established based on cellular communications between target monitor 120 and a cellular communication system 150. Furthermore, when wireless communication link 133 between target monitor 120 and cellular communications system 150 is periodically established, at those times, target monitor 120 may report status and other stored records including location fixes to a central monitoring system 160 via wireless communication link 138.

Monitoring system 100 includes, but is not limited to, at least one beacon 180. Beacons 180 are instrumental for beacon based monitoring systems. Within FIG. 1, a telemetric wireless link 141 has been depicted between beacon 180a and target monitor 120. Each beacon 180 has an adjustable range to make telemetric wireless contact with target monitor 120. At any point in time, depending on each beacon's 180 relative distance to target monitor 120, none, one, or more than one tracking beacons 180 may be within transmission range of a single target monitor 120. Likewise, it is further conceivable under various circumstances that more than one target monitor 120 at times be within in range of a solitary beacon 180.

Telemetric wireless communications path 141 established at times between tracking beacon 180a and target monitor 120 illustrates a common feature of various different embodiments of the current invention. Some embodiments of the various inventions vary on how, i.e. protocol, and what information and/or signaling is passed over wireless link 141. For example, in more simplified configurations and embodiments, each beacon 180 is limited to repetitively transmitting its own beacon ID and physical location information. In that way, once target monitor 120 is within transmission range of tracking beacon 180a and establishes wireless or wired reception 141, then target monitor 120 can record and store received beacon ID and location information. At a later time, for some embodiments of the present invention, target monitor 120 can then report recorded readings from beacons 180 to the central monitoring system 160 over the cellular communication system 150 using wireless links 133 and 138 as depicted in FIG. 1. Furthermore, many embodiments allow for such transmissions and information passing to occur without being noticed by human subject 110, and unnoticed, automatically, and near effortlessly central monitoring system 160 is able to establish records and track human subject's 110 movements and whereabouts.

In other embodiments or configurations according to the present invention, each beacon 180 also transmit status information related to its own device health and information related from each beacon's 180 internal tampering, movement, or other sensors via a communication system 170 to central monitoring system 160. This allows for detection of movement of beacons 180, and establishing some level of confidence that the location reported by each of beacons 180 is accurate. Various other details about a beacon based system are disclosed in U.S. patent application Ser. No. 12/041,746 entitled "Beacon Based Tracking Devices and Methods for Using Such" and filed Mar. 4, 2008 by Buck et al. The entirety of the aforementioned reference is incorporated herein by reference for all purposes.

Likewise, in some other embodiments, each target monitor 120 contains a host of their own power status, tampering, shielding, movement, and/or other sensors related to its own device health. While still further embodiments also include a host of other measurement transducers within target monitor 120 for extracting information, and for later reporting, related to physical properties of human subject 110. For example, measuring for the presence of alcohol and/or other drugs present in human subject 110 may be included in some embodiments of target monitor 120. As one example, the alcohol sensor discussed in U.S. Pat. No. 7,930,927 entitled "Transdermal Portable Alcohol Monitor and Methods for Using Such" and filed by Cooper et al. on Mar. 4, 2008. The entirety of the aforementioned reference is incorporated herein by reference for all purposes.

Beacons 180 in alternative embodiments of the present invention may communicate with central monitoring system 160 independently of target monitor 120. The monitoring system 100 illustrated in FIG. 1a shows beacon 180b having both a wireless communication link 135 with cellular communication system 150, and also illustrates beacon 180b having a hardwired communication link 139 with land communication system 170. Monitoring system 100 is also shown with beacons 180a, 180b, and 180c each having hardwired land communication links 140, 139, and 136 respectively to land communication system 170. Monitoring system 100 further illustrates land communication system 170 having a hardwired communication link 134 to cellular communication system 150, and a hardwired communication link 137 to central monitoring system 160.

In some embodiments of the present invention, beacons 180 are located in areas frequented by human subject 110 where target monitor 120 is incapable of accessing information from the GPS system. Such beacons eliminate the need to perform an AFLT fix and avoid the costs associated therewith. As an example, human subject 110 may have a tracking beacon 180 placed within his home, and one also placed at his place of employment in close proximity to his work area. In this way, the two placed beacons, each at different prescribed times, can interact with his attached target monitor 120 to periodically make reports to central monitoring system 160 to track movements and the whereabouts of human subject 110. All this can be done without incurring the costs associated with performing an AFLT fix.

Monitoring system 100 further includes a control station 191 that is communicably coupled to central monitoring system 160 via a communication link 192. In one particular embodiment of the present invention, control station 191 is a personal computer including a display device, a processor, and/or one or more I/O devices. Based upon the disclosure provided herein, one of ordinary skill in the art will recognize a variety of systems that may be used as control station 191 including highly tailored application specific control systems. A storage medium 194 is communicably coupled to control station 191 and maintains instructions governing the operation of pursuit mode control in relation to central monitoring system 160 and target monitor 120.

Central monitoring system 160 includes functionality for sending alerts to a user interaction system 185 when a tracked target ventures into a prohibited zone as updated by the adaptive zone update control, for providing location information indicating a location of target monitor 120, and/or for receiving a request to place target monitor 120 into a pursuit mode. Various implementations of the pursuit mode control implemented across central monitoring system 160 and target monitor 120 are more fully described below in relation to FIGS. 2-6 below. User interaction system 185 may be, but is not limited to, a law enforcement computer deployed at a dispatch station of the law enforcement facility or a hand held computer maintained by a law enforcement official. Based upon the disclosure provided herein, one of ordinary skill in the art will recognize a variety of user interaction systems 185 that may be used in relation to one or more of the embodiments discussed herein. Further, it should be noted that such a system is not limited to use in relation to law enforcement.

Figure 1B:
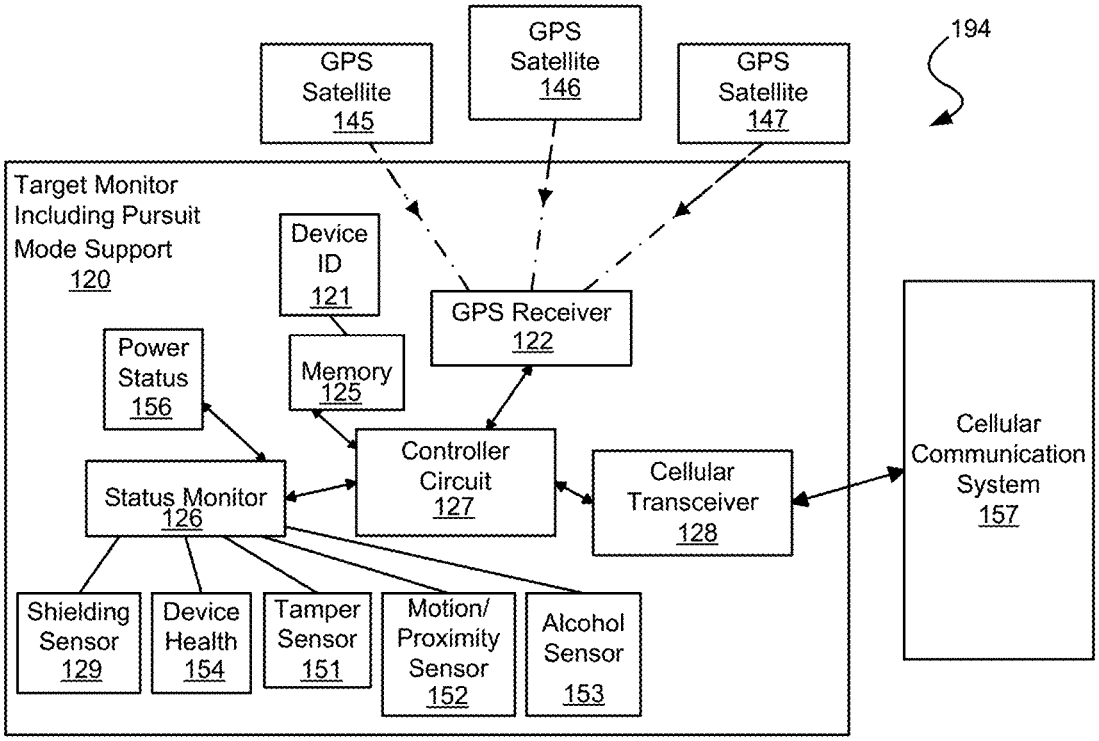
FIG. 1b is a block diagram of a target monitor device including pursuit mode support in accordance with one or more embodiments of the present invention.

Turning to FIG. 1b, a block diagram 194 of target monitor device 120 including pursuit mode support is shown in accordance with one or more embodiments of the present invention. As shown, target monitor device 120 includes a device ID 121 that may be maintained in a memory 125, and thus is accessible by a controller circuit 127. Controller circuit 127 is able to interact with GPS receiver 122 and memory 125 at times for storing and generating records of successively determined GPS locations. Where target monitor 120 is operating in a standard mode, controller circuit 127 causes an update and reporting of the location of target monitor device via a cellular transceiver 128 and a cellular communication system 157 in accordance with a first time period. In contrast, where target monitor 120 is operating in a pursuit mode, controller circuit 127 causes an update and reporting of the location of target monitor device via cellular transceiver 128 and cellular communication system 157 in accordance with a second time period. The second time period is substantially shorter than the first time period. In one particular embodiment of the present invention, the first time period is approximately three minutes and the second time period is approximately every fifteen seconds. Based upon the disclosure provided herein, one of ordinary skill in the art will recognize other durations for the first time period and the second time period in accordance with different embodiments of the present invention. In some embodiments of the present invention, one or both of the first time period and the second time period is/are user programmable. Operating target monitor device 120 in the pursuit mode consumes substantially more power than in the standard mode. Controller circuit 127 may be, but is not limited to, an application specific circuit configured to perform control functions for target monitor. Memory 125 may be any type of memory known in the art such as, for example, a EEPROM or RAM memory. In some cases where controller circuit 127 executes instructions, such instructions may be maintained in memory 125.

Controller circuit 127 of target monitor 120 at times functions in conjunction with cellular transceiver 128 to send and receive data and signals through cellular communication system 190. This link at times is useful for passing information and/or control signals between a central monitoring system (not shown) and multi-purpose monitoring device 120. The information transmitted may include, but is not limited to, location information, alcohol information, and information about the status of multi-purpose monitoring device 120. Based on the disclosure provided herein, one of ordinary skill in the art will recognize a variety of information that may be transferred via cellular communication system 190.

Various embodiments of target monitor 120 include a variety of sensors capable of determining the status of target monitor 120, and of the individual associated therewith. For example, a status monitor 126 may include one or more of the following subcomponents: a power status sensor 156 capable of indicating a power status of target monitor 120. The power status may be expressed, for example as a percentage of battery life remaining. Based upon the disclosure provided herein, one of ordinary skill in the art will recognize a variety of forms in which power status may be expressed. In addition, target monitor 120 includes a set of shielding sensors 129 that are capable of determining whether target monitor 120 is being shielded from receiving GPS signals and/or if GPS jamming is ongoing, a set of device health indicators 154, a tamper sensor 131 capable of determining whether unauthorized access to target monitor 120 has occurred or whether target monitor 120 has been removed from an associated human subject, a motion/proximity sensor 152 capable of determining whether target monitor 120 is moving and/or whether it is within proximity of an individual associated with target monitor 120, and/or an alcohol sensor 153 such as that described herein. Based on the disclosure provided herein, one of ordinary skill in the art will recognize a variety of shielding sensors, a variety of device health transducers and indicators, a variety of tamper sensors, various different types of motion sensors, different proximity to human sensors, and various human body physical measurement sensors or transducers that may be incorporated into target monitor 120 according to various different instances and/or embodiments of the present invention.

Figure 1C:
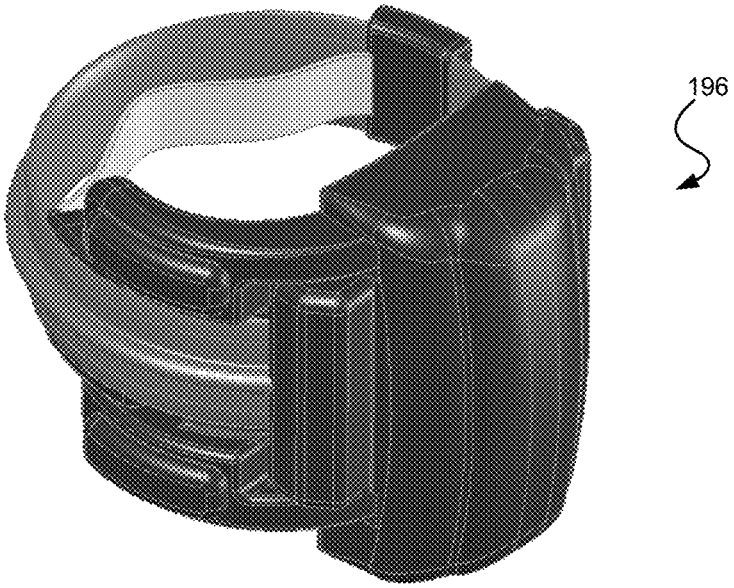
FIG. 1c shows a target monitor device including pursuit mode support in accordance with one or more embodiments of the present invention.

Turning to FIG. 1c, one implementation 196 of a combination of target monitor 120 and strap 190 is shown in accordance with one or more embodiments of the present invention.

Figure 2:
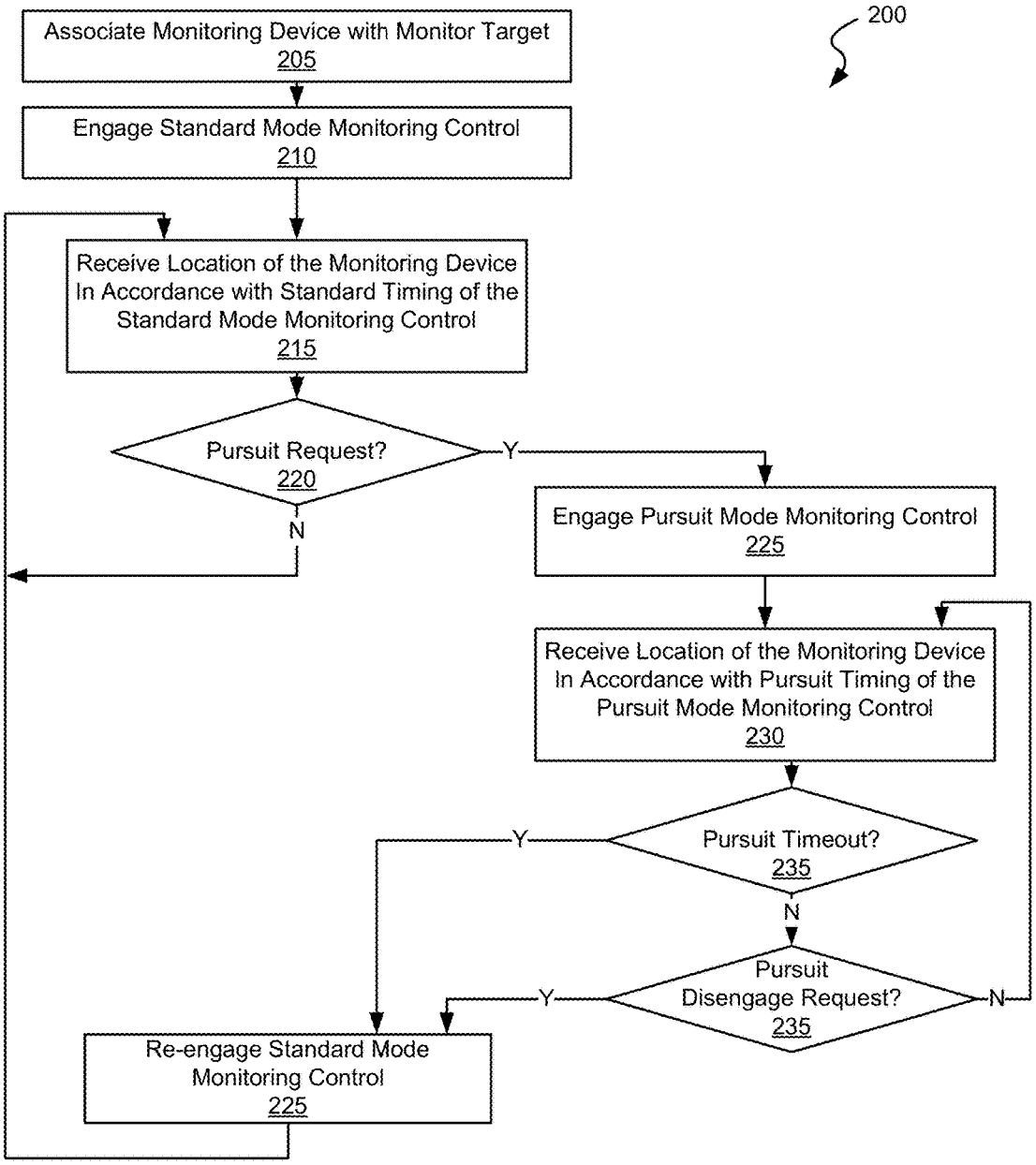
FIG. 2 is a flow diagram depicting a method for selective pursuit mode monitoring in accordance with some embodiments of the present invention.

Turning to FIG. 2, a flow diagram 200 depicts a method for selective pursuit mode monitoring in accordance with various embodiments of the present invention. Following flow diagram 200, a monitor device is associated with a monitor target (block 205). Where the monitor target is a human subject, associating the monitor device with the monitor target may include placing the monitor device in a pouch maintained by the human subject or physically attaching the monitoring device to the human subject using, for example, a strap or bracelet. Alternatively, where the monitor target is a non-human asset, associating the monitor device with the monitor target may include placing the monitor device inside the target or otherwise attaching the monitor device to the target. Based upon the disclosure provided herein, one of ordinary skill in the art will appreciate a variety of ways that a monitor device may be associated with a target.

Initially standard mode monitoring control is engaged (block 210). Standard mode monitoring control requires monitor device 120 to update its location and report the location based upon a first time period. Such updating includes monitor device 120 enabling location circuitry at the end of each repeat of the first period to obtain location information, and enabling communication circuitry to transmit the location information to central monitoring system 160. The first time period may either be fixed or user programmable, and is selected as a balance between extending the battery life of target monitor 120 and providing a reasonably updated indication of the location of target monitor 120. In one particular embodiment of the present invention, the first period is approximately three minutes. Based upon the disclosure provided herein, one of ordinary skill in the art will recognize other periods that may be used in relation to different embodiments of the present invention.

With the standard mode monitoring control engaged (block 210), location information from the monitor device is received in accordance with the standard timing (i.e., repetitively at the end of completion of the first period) (block 215). Such reception of location information includes central monitoring system 160 receiving location information from target monitor 120 via cellular communication system 190 at the end of completion of each of the first period. It should be noted that other communication links such as WiFi may be used in relation to other embodiments of the present invention.

It is determined whether a request to operate in pursuit mode has been received (block 220). Such a request to operate in pursuit mode may be received from, for example, user interaction system 185. Where a request to operate in pursuit mode has not been received (block 220), processing continues in accordance with the standard timing of the standard mode monitoring control.

Alternatively, where a request to operate in pursuit mode has been received (block 220), pursuit mode monitoring control is engaged (block 225). Pursuit mode monitoring control requires monitor device 120 to update its location and report the location based upon a second time period. Such updating includes monitor device 120 enabling location circuitry at the end of each repeat of the second period to obtain location information, and enabling communication circuitry to transmit the location information to central monitoring system 160. The second time period may either be fixed or user programmable, and modifies the balance between extending the battery life of target monitor 120 and providing a reasonably updated indication of the location of target monitor 120 of the first time period such that an updated indication of the location of target monitor is received more often at the expense of the battery life of target monitor 120. In one particular embodiment of the present invention, the second period is approximately fifteen seconds. Based upon the disclosure provided herein, one of ordinary skill in the art will recognize other periods that may be used in relation to different embodiments of the present invention.

With the pursuit mode monitoring control engaged (block 225), location information from the monitor device is received in accordance with the pursuit timing (i.e., repetitively at the end of completion of the second period) (block 230). Such reception of location information includes central monitoring system 160 receiving location information from target monitor 120 via cellular communication system 190 at the end of completion of each of the second period. Again, it should be noted that other communication links such as WiFi may be used in relation to other embodiments of the present invention.

It is determined whether a pursuit time out condition has occurred (block 235). To avoid target monitor device 120 being left in pursuit mode and thereby prematurely exhausting its battery life, a time expiration is set when target monitor device 120 is initially placed in pursuit mode. Once the period of the time expiration passes as determined by a timer either in central monitoring system 160 or target monitor 120 (i.e., it is determined that the pursuit time out condition has occurred (block 235)), standard mode monitoring control is re-engaged (block 225). The re-engaging is done similar to that discussed above in relation to block 210.

Alternatively, where it is determined that a pursuit time out condition has not occurred (block 235), it is determined whether a pursuit disengage request has been received (block 240). Such a request to disengage may be received from, for example, user interaction system 185. Where a request to disengage has not been received (block 240), processing continues in accordance with the standard timing of the pursuit mode monitoring control. Otherwise, where a request to disengage has been received (block 240), standard mode monitoring control is re-engaged (block 225).

Figure 3:
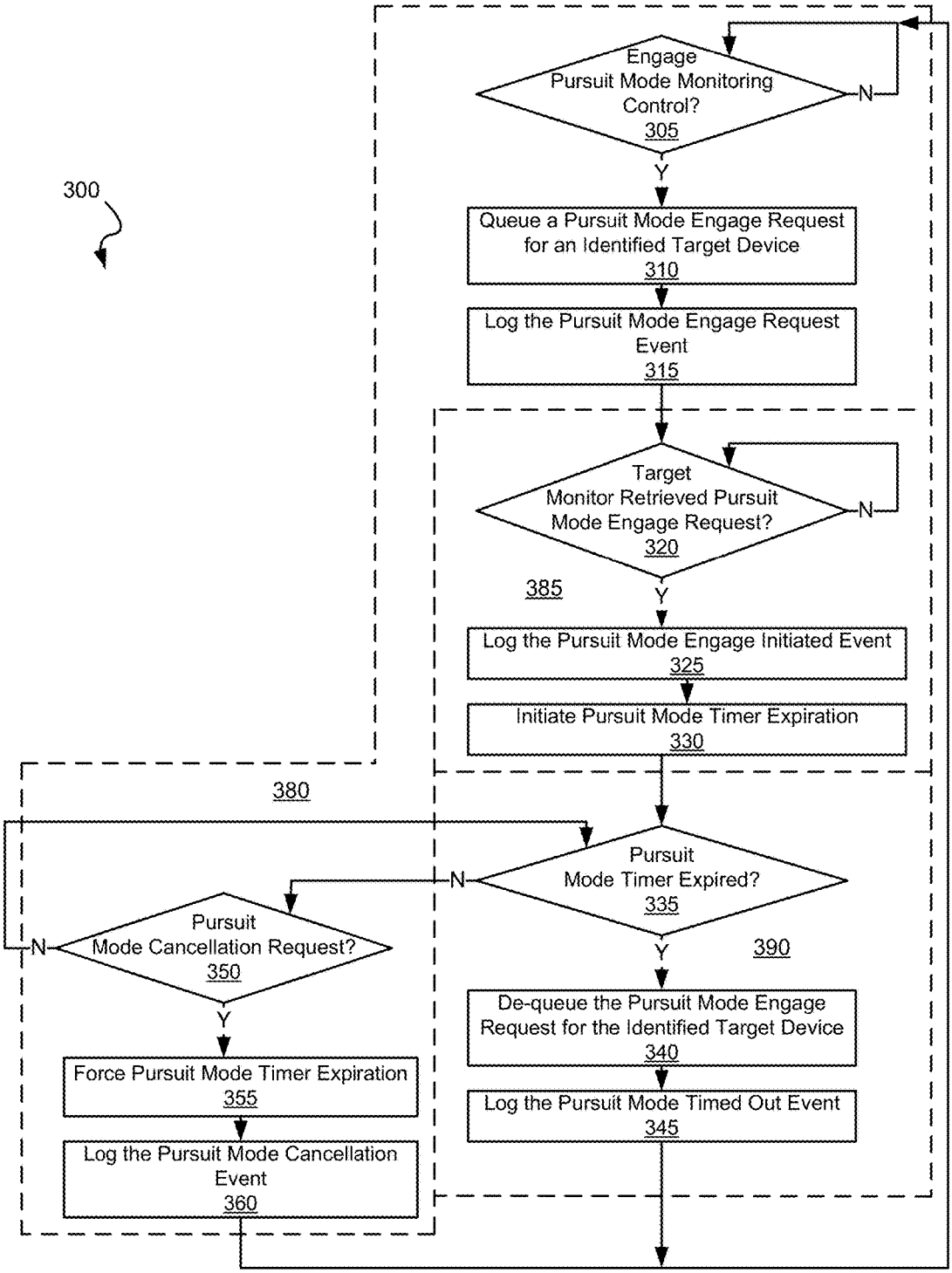
FIG. 3 is a flow diagram showing a method for initiating a target monitor device in accordance with various embodiments of the present invention.

Turning to FIG. 3, a flow diagram 300 shows a method for initiating a target monitor device in accordance with various embodiments of the present invention. Three basic processing blocks are implemented by central monitoring system 160: user interface command processing 380 (outlined in dashed lines), command queue processing 385 (outlined in dashed lines), and pursuit mode time out processing 390 (outlined in dashed lines). Following flow diagram 300, it is determined whether the target monitor is to be engaged in pursuit mode (block 305). The determination may be based, for example, by whether a request for pursuit mode has been received by central monitoring system 160 via user interaction system 185. Where the target monitor is to be engaged in pursuit mode (block 305), a pursuit mode engage request is queued for the identified target monitor (block 310). This may include, for example, writing a pursuit mode engage request in a queue maintained by central monitoring system 160 where it awaits a read by the particular target monitor 120. As another example, this may include transmitting an update to the particular target monitor 120 which accepts the update to a queue maintained by target monitor 120. The request to engage in pursuit mode is logged in central monitoring system 160 as a pursuit mode engage request event (block 315).

It is then determined whether the target monitor retrieved the pursuit mode engage request (block 320). Where the pursuit mode request has been retrieved (block 320), it is assumed that the pursuit mode has been engaged by the particular target monitor and as such a pursuit mode engage initiated event is logged by central monitoring system 160 (block 325). A pursuit mode timer expiration is initiated (block 330). The pursuit mode timer is programmed for a maximum time to allow target monitor to operate in pursuit mode. After initiation, the pursuit mode timer begins to count indicating the time that target monitor 120 is in the pursuit mode. Absent a command to leave the pursuit mode, target monitor 120 continues to operate in the pursuit mode until the pursuit mode timer expires.

It is determined whether the pursuit mode timer has expired (block 335). Again, absent a command to leave the pursuit mode, target monitor 120 continues to operate in the pursuit mode until the pursuit mode timer expires (block 335). Alternatively, where the pursuit mode timer has expired (block 335), the pursuit mode engage request (originally written in block 310) is de-queued (block 340) and a pursuit mode timed out event is logged (block 345). This causes target monitor 120 to revert back to standard mode operation.

Where the pursuit mode timer has not yet expired (block 335), it is determined whether a request to cancel the pursuit mode has been received (block 350). The determination may be based, for example, by whether a request to cancel the pursuit mode has been received by central monitoring system 160 via user interaction system 185. Where a cancellation request has been received (block 350), a pursuit mode timer expiration is forced (block 355) and a pursuit mode cancellation event is recorded (block 360). This causes target monitor 120 to revert back to standard mode operation.

Figure 4:
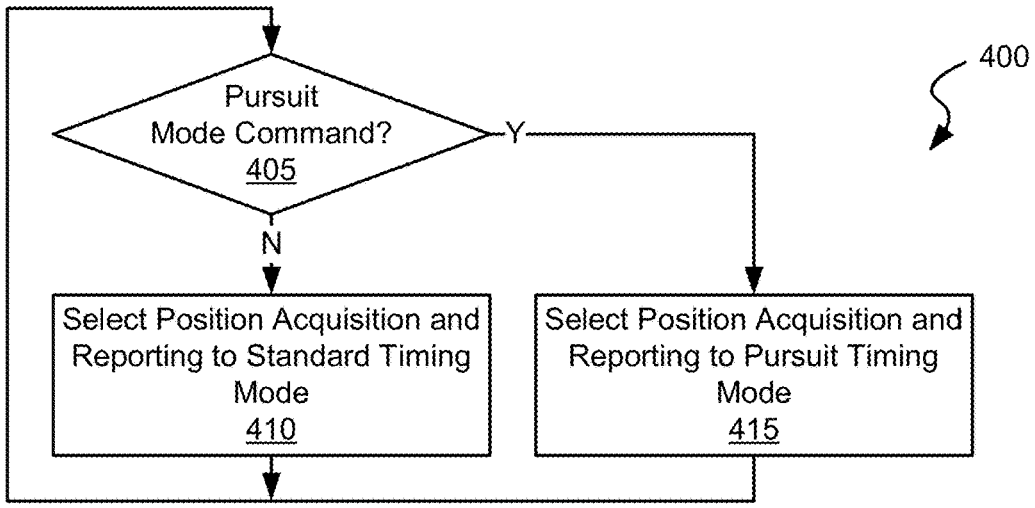
FIG. 4 is a flow diagram depicting a method for target device switching in accordance with some embodiments of the present invention.

Turning to FIG. 4, a flow diagram 400 depicts a method for target device switching in accordance with some embodiments of the present invention. Following flow diagram 400, target monitor 120 determines whether it has received a command to enter the pursuit mode (block 405). This command is received from central monitoring system 160 via cellular communication system 150. Where a pursuit mode command is received (block 405), position acquisition and reporting is selected to conform to the timing of the pursuit mode (block 415). Otherwise, position acquisition and reporting is selected to conform to the timing of the standard mode (block 410).

Figure 5:
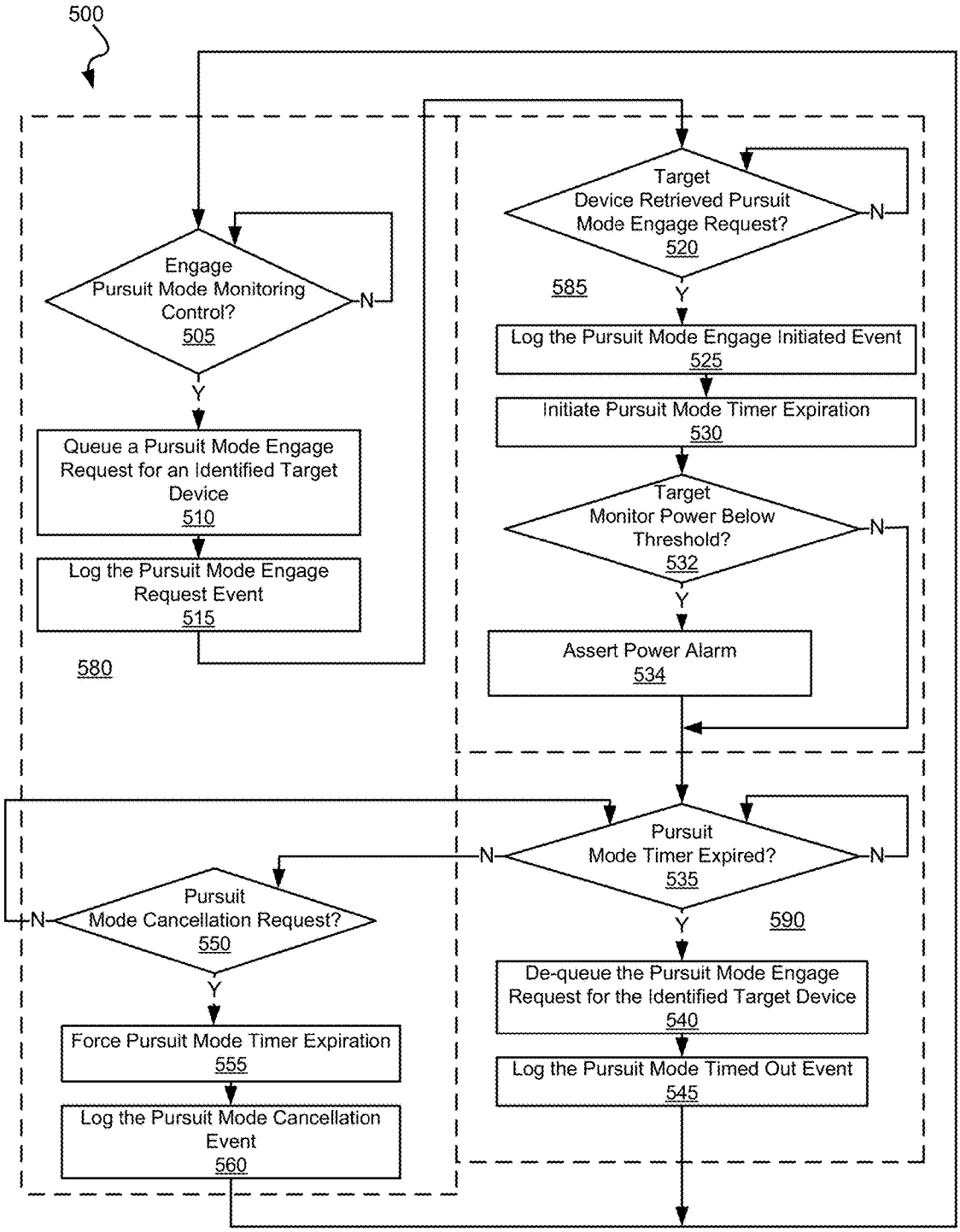
FIG. 5 is a flow diagram showing another method for initiating a target monitor device in accordance with various embodiments of the present invention.

Turning to FIG. 5, a flow diagram 500 shows another method for initiating a target monitor device in accordance with various embodiments of the present invention. Three basic processing blocks are implemented by central monitoring system 160: user interface command processing 580 (outlined in dashed lines), command queue processing 585 (outlined in dashed lines), and pursuit mode time out processing 590 (outlined in dashed lines). Following flow diagram 500, it is determined whether the target monitor is to be engaged in pursuit mode (block 505). The determination may be based, for example, by whether a request for pursuit mode has been received by central monitoring system 160 via user interaction system 185. Where the target monitor is to be engaged in pursuit mode (block 505), a pursuit mode engage request is queued for the identified target monitor (block 510). This may include, for example, writing a pursuit mode engage request in a queue maintained by central monitoring system 160 where it awaits a read by the particular target monitor 120. As another example, this may include transmitting an update to the particular target monitor 120 which accepts the update to a queue maintained by target monitor 120. The request to engage in pursuit mode is logged in central monitoring system 160 as a pursuit mode engage request event (block 515).

It is then determined whether the target monitor retrieved the pursuit mode engage request (block 520). Where the pursuit mode request has been retrieved (block 520), it is assumed that the pursuit mode has been engaged by the particular target monitor and as such a pursuit mode engage initiated event is logged by central monitoring system 160 (block 525). A pursuit mode timer expiration is initiated (block 530). The pursuit mode timer is programmed for a maximum time to allow target monitor to operate in pursuit mode. After initiation, the pursuit mode timer begins to count indicating the time that target monitor 120 is in the pursuit mode. Absent a command to leave the pursuit mode, target monitor 120 continues to operate in the pursuit mode until the pursuit mode timer expires.

As discussed more fully below in relation to FIG. 6, target monitor 120 reports battery status back to central monitoring system 160. Using this battery status, central monitoring system 160 determines whether the remaining battery life of target monitor 120 is below a threshold (block 532). This threshold may either be fixed or user programmable. Where the target monitor power is below the threshold (block 532), a power alarm is asserted (block 534). This power alarm may warn of an exhaustion of the battery in target monitor 120 within a specified period.

It is determined whether the pursuit mode timer has expired (block 535). Again, absent a command to leave the pursuit mode, target monitor 120 continues to operate in the pursuit mode until the pursuit mode timer expires (block 535). Alternatively, where the pursuit mode timer has expired (block 535), the pursuit mode engage request (originally written in block 510) is de-queued (block 540) and a pursuit mode timed out event is logged (block 545). This causes target monitor 120 to revert back to standard mode operation.

Where the pursuit mode timer has not yet expired (block 535), it is determined whether a request to cancel the pursuit mode has been received (block 550). The determination may be based, for example, by whether a request to cancel the pursuit mode has been received by central monitoring system 160 via user interaction system 185. Where a cancellation request has been received (block 550), a pursuit mode timer expiration is forced (block 555) and a pursuit mode cancellation event is recorded (block 560). This causes target monitor 120 to revert back to standard mode operation.

Figure 6:
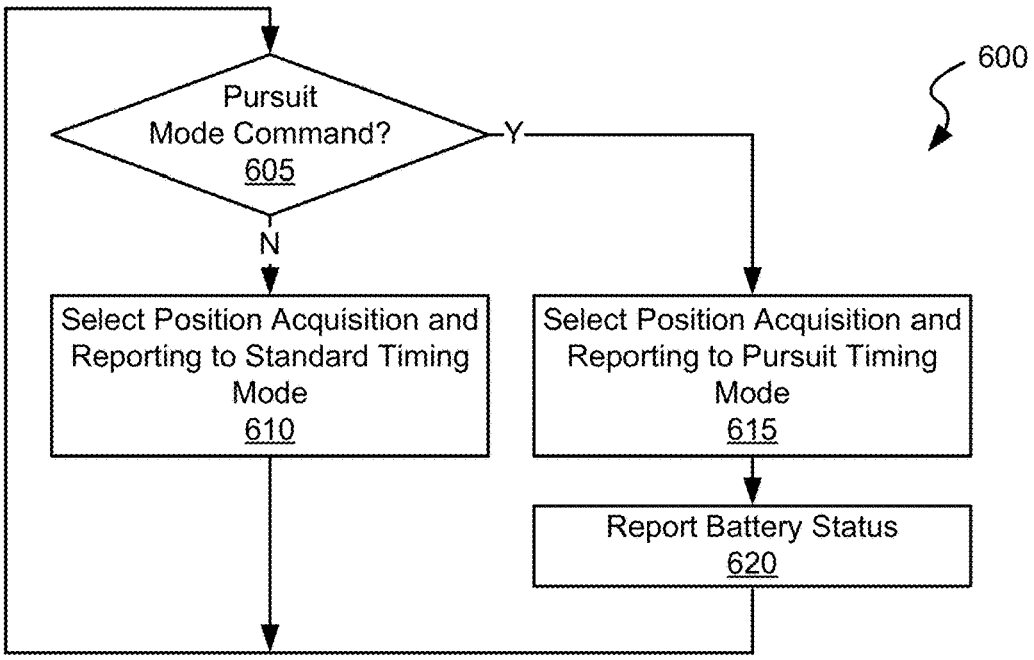
FIG. 6 is a flow diagram depicting another method for target device switching in accordance with some embodiments of the present invention.

Turning to FIG. 6, a flow diagram 600 depicts another method for target device switching in accordance with some embodiments of the present invention. Following flow diagram 600, target monitor 120 determines whether it has received a command to enter the pursuit mode (block 605). This command is received from central monitoring system 160 via cellular communication system 150. Where a pursuit mode command is received (block 605), position acquisition and reporting is selected to conform to the timing of the pursuit mode (block 615) and the battery status of target monitor 120 is reported back to central monitoring system 160 (block 620). Otherwise, position acquisition and reporting is selected to conform to the timing of the standard mode (block 610).

In conclusion, the present invention provides for novel systems, devices, and methods for monitoring individuals and/or assets. While detailed descriptions of one or more embodiments of the invention have been given above, various alternatives, modifications, and equivalents will be apparent to those skilled in the art without varying from the spirit of the invention. Therefore, the above description should not be taken as limiting the scope of the invention, which is defined by the appended claims.

What is claimed is:

1. A monitoring system, the monitoring system comprising:

*a monitoring device; and* a central monitoring apparatus [operable] *configured* to:

receive a user request to engage a pursuit mode; and generate a request to modify operation of [a] *the* monitoring device;

*wherein* the monitoring device [including] *includes*:

a location determination circuit [operable] *configured* to update a location of the [monitor] *monitoring* device in accordance with a location update mode; and a controller circuit [operable] *configured* to:

receive the request to modify operation of the monitoring device;

modify the location update mode from a first update mode to a pursuit update mode, wherein a rate of update in the pursuit update mode is different from a rate of update in the first update mode;[and]

report the location of the [monitor] *monitoring* device to the central monitoring apparatus*; and*

*modify the location update mode from the pursuit update mode to the first update mode upon expiration of a defined maximum duration of operating the monitoring device in the pursuit update mode*.

2. The monitoring system of claim 1, wherein the pursuit update mode includes an automatic update at the rate *of update in the pursuit update mode.*

3. The monitoring system of claim 2, wherein the rate *of update in the pursuit update mode* is once every fifteen seconds.

4. The monitoring system of claim 2, wherein the rate *of update in the pursuit update mode* is a second rate, wherein the first update mode includes an automatic update at a first rate, and wherein the first rate is less than the second rate.

5. The monitoring system of claim 4, wherein the first rate is once every three minutes, and wherein the second rate is once every fifteen seconds.

6. The monitoring system of claim 1, wherein the central monitoring apparatus is further [operable] *configured* to receive the location of the [monitor] *monitoring* device reported by the [monitor] *monitoring* device.

[7. The monitoring system of claim 6, wherein the central monitoring apparatus is further operable to set a timeout condition corresponding to a maximum duration of operating the monitoring device in the pursuit update mode.]

[8. The monitoring system of claim 1, wherein the controller circuit is futher operable to modify the location update mode from the pursuit update mode to the first update mode upon expiration of a defined maximum duration of operating the monitoring device in the pursuit update mode.]

9. The monitoring system of claim [8] *1*, wherein the defined maximum duration is greater than thirty minutes.

10. The monitoring system of claim 1, wherein the controller circuit is further [operable] *configured* to:

update a power status of the monitoring device; and report the power status to [a] *the* central monitoring apparatus.

11. The monitoring system of claim 10, wherein the central monitoring apparatus is further [operable] *configured* to:

compare the power status of the monitoring device with a threshold value; and provide a power status alert to a user where a combination of a power status being below the threshold value and modification of the [schedule of location updates] *location update mode* from the first update mode to the pursuit update mode [schedule has been implemented].

12. The monitoring system of claim 1, wherein the monitoring device is a single piece device, and wherein the monitoring system further comprises:

a strap configured to attach the [monitor] *monitoring* device to a target.

13. The monitoring system of clam 1, wherein the location determination circuit is further [operable] *configured* to identify a direction of movement of the monitoring device, and wherein *the controller circuit is further configured to*

*report* the direction of movement of the monitoring device [is reported] when the monitoring device is operating in the pursuit update mode.

14. The monitoring system of claim 1, wherein the location determination circuit includes global positioning system circuitry.

15. The monitoring system of claim 1, wherein the location determination circuit includes cell tower triangulation circuitry.

16. The monitoring system of claim 1, wherein the monitoring system further comprises:

a user interaction system [operable] *configured* to receive a command from a user, and wherein the user request to engage the pursuit update mode corresponds to the command from the user.

17. The monitoring system of claim [1] *16*, wherein the user interaction system is further [operable] *configured* to provide information about the monitoring device to the user.

18. The monitoring system of claim 1, wherein *the controller circuit includes cellular network communication circuitry, and wherein* the request to modify operation of the monitoring device is received by the [monitor] *monitoring* device via [a] *the* cellular [network] *communication circuitry*.

19. A monitoring device including:

[a strap configured for attaching to a target;]

a location determination circuit [operable] *configured* to update a location of [the] *a* target at a selected update rate; and a controller circuit communicably coupled to a user request station, and [operable] *configured* to:

receive a request to modify the selected update rate from a first rate to a second rate, wherein the first rate is less than the second rate, and wherein the request to modify is based at least in part on a user request received via the user request station; [and]

increase a rate of reporting the location of the [monitor] *monitoring* device in accordance with the request to modify; *and*

*cause a decrease in the rate of updating and reporting the location upon expiration of a defined maximum duration of operating the monitoring device at the second rate*.

20. A monitoring system, the monitoring system comprising:

a monitoring device including:

a location determination circuit [operable] *configured* to update a location of the [monitor] *monitoring* device in accordance with a location update mode; and a controller circuit communicably coupled to a user request station, and [operable] *configured* to:

receive a request to modify operation of the monitoring device, wherein the request to modify is based at least in part on a user request received via the user request station;

modify the location update mode from a first update mode to a pursuit update mode, wherein a rate of update in the pursuit update mode is different from a rate of update in the first update mode; [and]

report the location of the [monitor] *monitoring* device to a central monitoring apparatus*; and*

*modify the location update mode from the pursuit update mode to the first update mode upon expiration of a defined maximum duration of operating the monitoring device in the pursuit update mode.*

[21. A monitoring system, the monitoring system comprising:

a central monitoring apparatus operable to:

generate a request to modify operation of a monitoring device; and receive a location of the monitor device;

the monitoring device including:

a location determination circuit including global positioning system circuitry and operable to update the location of the monitor device in accordance with a location update mode; and a controller circuit operable to:

receive the request to modify operation of the monitoring device via a cellular network;

modify the location update mode from a first update mode to a pursuit update mode, wherein a rate of update in the pursuit update mode is different from a rate of update in the first update mode, and wherein the pursuit update mode includes an automatic update at the rate; and report the location of the monitor device to the central monitoring apparatus;

a user interaction system operable to:

receive a command from a user, wherein the request to modify operation of the monitoring device is generated in response to the command from the user; and provide information about the monitoring device monitoring system, the monitoring system comprising:

a monitoring device including:

a location determination circuit operable to identify a location of the monitoring device; and a controller circuit operable to:

receive a request to modify a schedule of location updates from a standard mode schedule to a pursuit mode schedule, wherein the standard mode schedule calls for updating the location of the monitoring device at a lower rate than the pursuit mode schedule; and cause an increase in the rate of updating and reporting the location in accordance with the request to modify.]

*22. The monitoring device of claim 19, wherein the second rate is once every fifteen seconds.*

*23. The monitoring device of claim 19, wherein the first rate is once every three minutes, and wherein the second rate is once every fifteen seconds.*

*24. The monitoring device of claim 19, wherein the defined maximum duration is greater than thirty minutes.*

*25. The monitoring device of claim 19, wherein the location determination circuit is further configured to identify a direction of movement of the monitoring device, and wherein the controller circuit is further configured to report the direction of movement of the monitoring device when the monitoring device is operating at the second rate.*

*26. The monitoring device of claim 19, wherein the location determination circuit includes satellite positioning system circuitry.*

*27. The monitoring system of claim 20, wherein the pursuit update mode includes an automatic update at the rate of update in the pursuit update mode.*

*28. The monitoring system of claim 27, wherein the rate of update in the pursuit update mode is once every fifteen seconds.*

*29. The monitoring system of claim 20, wherein the rate of update in the pursuit update mode is a second rate,*

*wherein the first update mode includes an automatic update at a first rate, and wherein the first rate is less than the second rate.*

*30. The monitoring system of claim 23, wherein the first rate is once every three minutes, and wherein the second rate is once every fifteen seconds.*

*31. The monitoring system of claim 30, wherein the defined maximum duration is greater than thirty minutes.*

*32. The monitoring system of claim 20, wherein the controller circuit is further configured to:*

*update a power status of the monitoring device; and*

*report the power status to a central monitoring apparatus.*

*33. The monitoring system of claim 20, wherein the monitoring system further comprises:*

*a strap configured to attach the monitoring device to a target.*

*34. The monitoring system of claim 20, wherein the location determination circuit is further configured to identify a direction of movement of the monitoring device, and wherein the controller circuit is further configured to report the direction of movement of the monitoring devicewhen the monitoring device is operating in the pursuit update mode.*

*35. The monitoring system of claim 20, wherein the location determination circuit includes satellite positioning system circuitry.*

*36. A monitoring system, the monitoring system comprising:*

*a monitoring device; and*

*a central monitoring apparatus configured to:*

*generate a request to modify operation of the monitoring device; and*

*set a timeout condition corresponding to a maximum duration of operating the monitoring device in a pursuit update mode;*

*wherein the monitoring device includes:*

*a location determination circuit configured to update the location of the monitoring device in accordance with a location update mode; and*

*a controller circuit configured to:*

*receive the request to modify operation of the monitoring device via a wireless communication link, wherein the request to modify operation of the monitoring device includes a request to modify the location update mode from a standard mode to the pursuit mode, and wherein a rate of location updates in the standard mode is less than a rate of location updates in the pursuit mode;*

*modify the location update mode from the standard mode to the pursuit mode, wherein the pursuit mode includes an automatic update at the rate of location updates in the pursuit mode; and*

*transmit the location of the monitoring device via the wireless communication link;*

*a user interaction system configured to:*

*receive a command from a user, wherein the request to modify operation of the monitoring device is generated in response to the command from the user; and*

*provide information about the monitoring device.*

*37. A monitoring device, the monitoring device comprising:*

*a location determination circuit configured to update a location of the monitoring device in accordance with an update rate; and*

*a controller circuit communicably coupled to a user request station and configured to:*

*receive a first request to modify the update rate, wherein the request to modify is based at least in part on a user request received via the user request station;*

*modify the update rate from a first rate to a second rate based at least in part on the first request to modify the update rate; and*

*subsequent to modifying the update rate from the first rate to the second rate based at least in part on the first request to modify the update rate, modify the update rate from the second rate to a third rate based at least in part upon expiration of a defined duration of operating the monitoring device at the second rate.*

*38. The monitoring device of claim 37, wherein the defined duration is greater than thirty minutes.*

*39. The monitoring device of claim 37, wherein the first rate is less than the second rate.*

*40. The monitoring device of claim 37, wherein the third rate is equal to the first rate.*

*41. The monitoring device of claim 37, wherein the controller circuit is further configured to:*

*coincident with modifying the update rate from the first rate to the second rate, modify a rate at which the monitoring device wirelessly transmits the location of the monitoring device.*

*42. The monitoring device of claim 37, wherein the monitoring device is included as part of a monitoring system, and wherein the monitoring system further includes:*

*a central monitoring device configured to receive the location of the monitoring device from the monitoring device.*

*43. The monitoring device of claim 37, wherein the location determination circuit is further configured to identify a direction of movement of the monitoring device, and wherein the controller circuit is further configured to wirelessly transmit the direction of movement of the monitoring device when updating the location of the monitoring device is done at the second rate.*

*44. The monitoring device of claim 37, wherein the monitoring device is included as part of a monitoring system, and wherein the monitoring system further includes:*

*a central monitoring device configured to generate the first request to modify the update rate based at least in part on a user request.*

*45. A monitoring device, the monitoring device comprising:*

*a location determination circuit configured to update a location of the monitoring device; and*

*a controller circuit communicably coupled to a user request station and configured to:*

*communicate the location of the monitoring device to a recipient device at an update rate;*

*receive a request to modify the update rate, wherein the request to modify is based at least in part on a user request received via the user request station;*

*modify the update rate from a first rate to a second rate based at least in part on the request to modify the update rate; and*

*subsequent to modifying the update rate from the first rate to the second rate based at least in part on the request to modify the update rate, modify the update rate from the second rate to a third rate based at least in part upon expiration of a time period.*

*46. The monitoring device of claim 45, wherein the first rate is the same as the third rate.*

* * * * *